United States Patent
Angelopoulos et al.

(10) Patent No.: US 9,921,167 B2
(45) Date of Patent: Mar. 20, 2018

(54) OPTICAL SENSOR BASED ON PFSI MEMBRANE COMPRISING ASSOCIATED BENZENE-1,3-DIOL FOR DETECTING TARGET COMPOUNDS, AND METHOD THEREOF

(71) Applicant: University of Cincinnati, Cincinnati, OH (US)

(72) Inventors: Anastasios Angelopoulos, Cincinnati, OH (US); Subasri M Ayyadurai, Cincinnati, OH (US); Jonathan A. Bernstein, Cincinnati, OH (US); Daniel S. Kanter, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 83 days.

(21) Appl. No.: 14/920,942

(22) Filed: Oct. 23, 2015

(65) Prior Publication Data

US 2016/0041105 A1     Feb. 11, 2016

Related U.S. Application Data

(63) Continuation-in-part of application No. 12/497,143, filed on Jul. 2, 2009, now abandoned.

(60) Provisional application No. 61/077,513, filed on Jul. 2, 2008.

(51) Int. Cl.
| | |
|---|---|
| *G01N 21/78* | (2006.01) |
| *G01N 31/22* | (2006.01) |
| *G01N 21/75* | (2006.01) |
| *G01N 21/77* | (2006.01) |

(52) U.S. Cl.
CPC ............. *G01N 21/78* (2013.01); *G01N 31/22* (2013.01); *G01N 2021/757* (2013.01); *G01N 2021/775* (2013.01)

(58) Field of Classification Search
CPC ..... B01D 69/10; B01D 69/06; Y10S 435/817; Y10S 435/917; Y10S 435/962; Y10S 977/943; Y10S 428/902; Y10S 977/775; Y10S 977/834; Y10S 977/882; B01J 2523/00
See application file for complete search history.

(56) References Cited

U.S. PATENT DOCUMENTS 6,130,101 A * 10/2000 Mao ..................... C07D 311/82
                                                     435/6.12

OTHER PUBLICATIONS

Baron and Elie "Temperature sensing using reversible thermochromic polymeric films", Sensors and Actuators, Sensors and Actuators B, 2003, v. 90, pp. 271-275.*
Michael and Ryer, "On the Action of Aldehydes on Phenols", American Chemical Journal, 1887, v. 5, pp. 130-137.*
Ayyadurai et al., "Perfluorosulfonic Acid Membrane Catalysts for Optical Sensing of Anhydrides in the Gas Phase", Anal. Chem., 2010, v. 82, No. 14, pp. 6265-6272.*

* cited by examiner

*Primary Examiner* — Yelena G Gakh
(74) *Attorney, Agent, or Firm* — Dinsmore & Shohl LLP

(57) ABSTRACT

An optical sensor for monitoring an environmental condition, the optical sensor comprising a perfluorosulfonate ionomer membrane comprising a solution, wherein the solution comprises a transition metal-free dye component, wherein exposure of the optical sensor to a specific environmental condition produces a color shift on the optical sensor.

10 Claims, 4 Drawing Sheets

OPTICAL SENSOR BASED ON PFSI MEMBRANE COMPRISING ASSOCIATED BENZENE-1,3-DIOL FOR DETECTING TARGET COMPOUNDS, AND METHOD THEREOF

CROSS REFERENCE TO RELATED APPLICATIONS

This application is a continuation-in-part of U.S. patent application Ser. No. 12/497,143, filed Jul. 2, 2009, which claims priority to U.S. Provisional Patent Application Ser. No. 61/077,513, filed Jul. 2, 2008, each of which is incorporated by reference in its entirety.

TECHNICAL FIELD

The present invention relates generally to optical sensors and methods of manufacturing optical sensors.

BACKGROUND OF THE INVENTION

Diacetyl (2,3-butanedione; $C_6H_6O_2$) and trimellitic anhydride ("TMA"; 1,3-dihydro-1,3-dioxo-5-isobenzofurancarboxylic acid; $C_9H_4O_5$) are toxic agents. Exposure to either may result in the development of respiratory illness or disease. Historically, optical detection and analysis of toxic agents has been more practical than other means for on-line continuous monitoring of hazardous levels because of the rapidity of the analysis. Optical detection and analysis of diacetyl has previously employed transitional metal complexes precipitated onto filters for visual inspection or applied to transparent films for ultraviolet-visible ("UV/VIS") spectroscopy. However, transitional metal complexes are expensive, difficult to prepare, and not sufficiently durable for continuous monitoring applications in clinical or manufacturing settings.

At present, there are no practical methods of rapid, on-line, continuous monitoring of either diacetyl or TMA levels.

There is a need in the industry for optical sensors capable of detecting the presence of diacetyl, TMA, and other elements or compounds, that are more durable, less expensive, and easier to manufacture than the spectroscopic filters and films currently available.

SUMMARY OF THE INVENTION

Accordingly, the present invention provides an optical sensor for monitoring an environmental condition.

One embodiment of the invention provides an optical sensor for monitoring an environmental condition, the optical sensor comprising a perfluorosulfonate ionomer ("PFSI") membrane comprising a solution, wherein the solution comprises a transition metal-free dye component, wherein exposure of the optical sensor to a specific environmental condition produces a color shift on the optical sensor.

Another embodiment of the invention provides a method of monitoring an environmental condition with an optical sensor comprising a perfluorosulfonate ionomer membrane comprising a solution, wherein the solution comprises a transition metal-free dye component, the method comprising the steps of exposing the optical sensor in an environment and examining the optical sensor for color shift associated with a specific environmental condition.

Another embodiment of the invention provides a method of manufacturing an optical sensor for monitoring an environmental condition, the method comprising the steps of: preparing a solution, wherein the solution comprises a transition metal-free dye component; immersing a perfluorosulfonate ionomer membrane in the solution; and removing the membrane after it has absorbed the solution.

DETAILED DESCRIPTION OF THE INVENTION

Definitions

Figure 1:
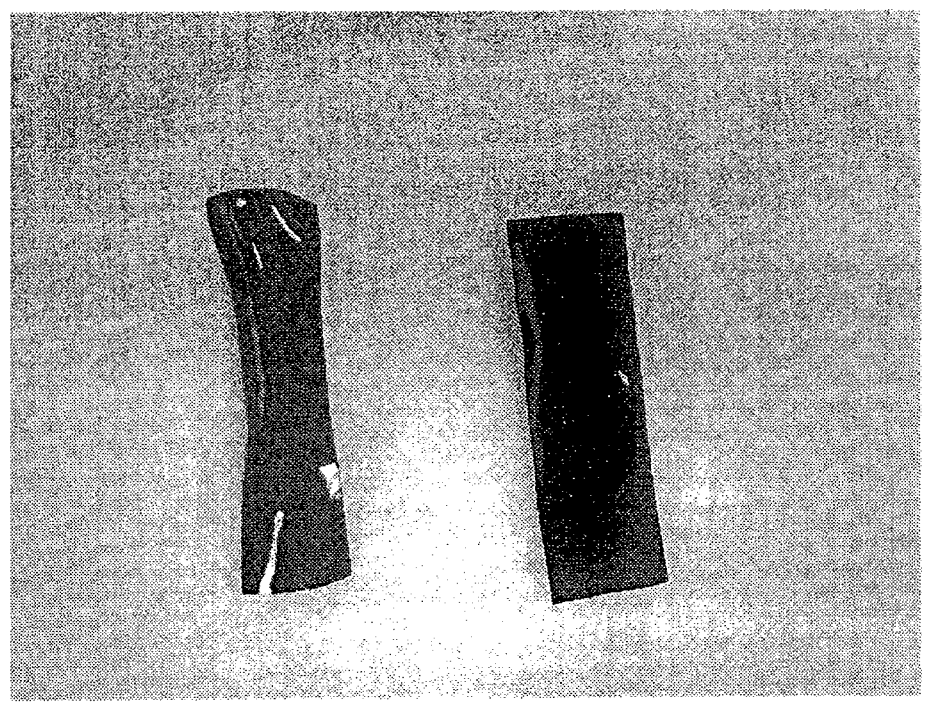
FIG. 1 is a black-and-white photograph of optical sensors comprising PFSI membranes and aromatic diamine before and after exposure to a glucose solution.

"Color shift" is a change in the absorption or reflection of electromagnetic radiation in the visible region of the electromagnetic spectrum. Color shift need not be detectable by the naked eye.

For example, exposure of an aromatic diamine dye to diacetyl in the presence of an acid catalyst results in an irreversible color shift of the aromatic diamine in the visible region of the electromagnetic spectrum. That is, aromatic diamine that has not been exposed to diacetyl in the presence of an acid catalyst is different in color than aromatic diamine that has been exposed.

Perfluorosulfonate ionomer ("PFSI") membranes provide media that can effectively and irreversibly absorb aromatic diamine from solution. The PFSI membrane provides support for the aromatic diamine dye and PFSI serves as the acid catalyst necessary to activate the aromatic diamine When exposed to diacetyl, the PFSI membrane comprising aromatic diamine exhibits an irreversible color shift, thereby serving as an optical sensor capable of effectively detecting the presence and relative concentration of diacetyl in an environment.

The optical sensor color is dependent upon the concentration of aromatic diamine in the optical sensor. The magnitude of the optical sensor's color shift upon exposure to diacetyl is dependent upon the concentration of aromatic diamine in the optical sensor, as well as the concentration of diacetyl in the environmental in which the optical sensor is exposed. The sensitivity of the optical sensor can be tuned for desired diacetyl concentrations and environments by adjusting the aromatic diamine concentration of the optical sensor. The optical sensor has exhibited sensitivity to diacetyl concentrations as low as parts per billion.

Optical sensors comprising PFSI membranes and aromatic diamine are also capable of detecting and discriminating, via color shift, among aldehydes and ketones that are chemically similar to diacetyl, such as vinyl acetate and 2,3-pentanedione.

Optical sensors comprising PFSI membranes and aromatic diamine also exhibit sensitivity to ionic platinum. Ionic platinum is anthropogenic and may pose a human health hazard. Metallic platinum serves as an electrocatalyst in proton exchange membrane ("PEM") fuel cell electrodes and is widely employed in automobile catalytic converters. The degradation and dissolution of metallic platinum during typical operation yields ionic platinum. Optical sensors comprising PFSI membranes and imbibed aromatic diamine may be used to monitor the degradation process. Information obtained during such monitoring may be used to improve electrode durability and mitigate beginning of life efficiency losses resulting from mass transport limitations.

Optical sensors comprising PFSI membranes and aromatic diamine also exhibit sensitivity to glucose. An unexposed optical sensor undergoes a color shift upon exposure to glucose. Detection of glucose with the optical sensor of this invention may be useful in human health monitoring and on-line monitoring of sugar content during biofuel processing.

PFSI membranes comprising aromatic diamine can also effectively sense pH levels. PFSI membranes can effectively absorb azo-based dyes from solutions containing azo-based dyes. When such membranes absorb azo-based dye, they become optical sensors capable of sensing pH levels via color shift. Optical sensors capable of sensing pH levels are important for monitoring breath condensate, an important mediator in asthma.

Exposure of an aromatic dye to an acid anhydride in the presence of an acid catalyst results in alteration of the electromagnetic absorption spectrum of the dye. An aromatic dye that has not been exposed to an anhydride in the presence of an acid catalyst is different in color than an aromatic that has been exposed to an anhydride in the presence of an acid catalyst.

PFSI membranes provide media that can effectively absorb benzene-1,3-diol (also known as resorcinol), from solution. The PFSI membrane provides support for the benzene-1,3-diol and also serves as the acid catalyst necessary to alter the light (electromagnetic) absorption spectrum of benzene-1,3-diol in the presence of an anhydride, such as TMA. When exposed to TMA, the PFSI membrane comprising the benzene-1,3-diol exhibits an irreversible color shift, thereby serving as an optical sensor capable of effectively detecting the presence and relative concentration of TMA in an environment.

Exposure of the optical sensor to solid or liquid TMA yields an optical response comparable to that exhibited by the optical sensor when exposed to the vapor phase of TMA.

Optical sensors comprising PFSI membranes and benzene-1,3-diol may also be used to effectively detect the presence and relative concentration of phthalic anhydride or maleic anhydride, via color shift.

The magnitude of the optical sensor's color shift upon exposure of the optical sensor to TMA, phthalic anhydride, or maleic anhydride is dependent upon the concentration of benzene-1,3-diol in the optical sensor, as well as the concentration of TMA, phthalic anhydride, or maleic anhydride in the environment to which the optical sensor is exposed. The sensitivity of the optical sensor can be tuned to detect lower or higher concentrations of anhydrides by adjusting the benzene-1,3-diol concentration of the optical sensor. The optical sensor has exhibited sensitivity to TMA, phthalic anhydride, or maleic anhydride concentrations as low as parts per billion.

The color shift associated with the presence of diacetyl, vinyl acetate, 2,3-pentanedione, TMA, phthalic anhydride, maleic anhydride, ionic platinum, or glucose or pH level may be detected with the naked eye. More detailed analysis of exposure over time is possible using spectroscopic analysis, which can analyze the color intensity variation over time. Such spectroscopic analysis can be performed on a real-time continuous basis using a portable monitor with light-emitting diode light sources and charge-coupled devices for analysis of the intensity of adsorbed and transmitted light. Alternatively, optical sensors may be collected periodically and analyzed at off-site spectrophotometers.

Figure 4:
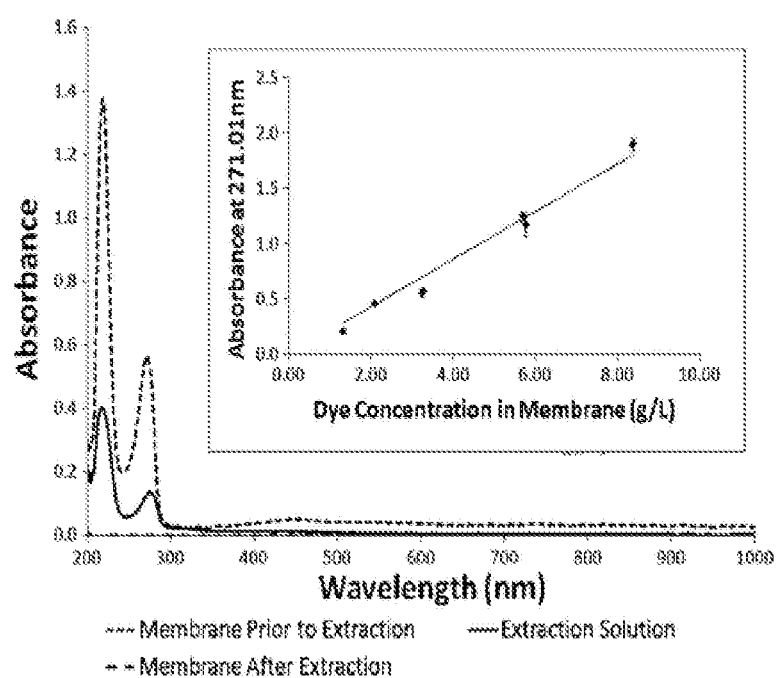
FIG. 4 is a graphical representation of a UV/vis spectra of resorcinol in extracted solution (dashed line) and in a PSA membrane before (solid line) and after (dashed line near zero absorbance) extraction, with the PSA background subtracted; the inset shows light absorption versus resorcinol membrane concentration.

As described above, the perfluorosulfonic acid membrane (PFSI) of the presently disclosed optical sensor operates as both a physical support and an acid catalyst for the specific reaction between the organic compound indicator and the target compound in the environment. Necessarily, the catalyst function of the PFSI membrane imposes a structural constraint on the sensor. The unique structural arrangement of molecular components in the solid state membrane permits highly selective optical detection of target compounds in the gas phase. For example, resorcinol (benzene-1,3-diol) is immobilized inside the PFSI membrane in a manner that permits close interaction with the perfluorosulfonic acid functional groups so as to take advantage of their catalytic activity in the solid state while not rendering them inactive. Evidence for the close association in the solid state exists in the form of the hypsochromic wavelength shift that is observed from 275.01 nm for the low intensity peak of resorcinol in ethanol-water solution to 271.22 nm in the PFSI membrane. This shift is accompanied by a reduction in the Beer-Lambert Law extinction coefficient from 2010 $m^2/g$ in ethanol-water solution to 1210 $m^2/g$ in the solid state membrane. Evidence is provided in FIG. 4, originally published by the present inventors in Ayyadurai, et al. "Perfluorosulfonic Acid Membrane Catalysts for Optical Sensing of Anhydrides in the Gas Phase," *Anal. Chem.* 82 (14): 6265-72 (2010) This material-specific data differentiates the presently disclosed optical sensors from alternate solid state approaches (e.g., powder mixing), wherein such coordination does not occur. Despite significant interaction and immobilization, resorcinol is still able to trap and coordinate with a target compound, which diffuses into the membrane from the gas phase in a manner that permits a chemical reaction to form an acylated product. The evidence for this highly specific reaction is the irreversible color shift, as defined and exemplified herein.

Despite significant interaction and immobilization, resorcinol is still able to trap and coordinate with a target compound (for example, trimellitic anhydride), which diffuses into the membrane from the gas phase in a manner that permits chemical reaction to form an acylated product. The result of this highly specific reaction is a color change visible on the PFSI membrane, which renders the presently disclosed device an optical sensor. In this way, the polymeric membrane serves as the bulk chemical reactor (and not merely as a support or separator) for optical sensing purposes. Prior to the instantly disclosed work, there was no expectation in the field of membrane chemistry that PFSI membrane could be used as both a support and a catalyst for highly specific detection of target molecules.

The close molecular association and structural alignment in the solid state between organic compound (e.g., aromatic diamine, an azo-based dye, and benzene-1,3-diol), perfluorosulfonic acid functional groups in the PFSI membrane, and target compound permits the perfluorosulfonic acid functional groups to catalyze the specific reaction between organic compound and target compound, giving rise to a color change on the PFSI membrane sensor. Regarding the term "close" with respect to molecular association and/or structural alignment, in certain embodiments the term "close" refers to association and/or alignment at the length scale of an atomic bond, often measured in Angstroms. In a specific embodiment, the organic compound, perfluorosulfonic acid functional group(s), and target compound are aligned along a length scale not greater than that typically associated with polar interactions (e.g., about 1 nm).

Exemplary embodiments of an optical sensor for monitoring an environmental condition are hereinafter described in detail in connection with the views and examples of FIGS. 1-2.

One exemplary embodiment of the invention comprises an optical sensor for monitoring an environmental condition comprising a perfluorosulfonate ionomer membrane comprising a solution, wherein the solution comprises a transition metal-free dye component, wherein exposure of the optical sensor to a specific environmental condition produces a color shift on the optical sensor.

In a specific exemplary embodiment of the optical sensor, the solution comprises aromatic diamine. In a more specific exemplary embodiment of the optical sensor the aromatic diamine comprises 3,4-diaminobenzophenone.

In another specific exemplary embodiment of the optical sensor, the solution comprises an azo-based dye.

In another specific exemplary embodiment of the optical sensor, the solution comprises benzene-1,3-diol.

In another specific exemplary embodiment of the optical sensor, the monitored specific environmental condition is the presence of diacetyl.

In another specific exemplary embodiment of the optical sensor, the monitored specific environmental condition is the presence of vinyl acetate.

In another specific exemplary embodiment of the optical sensor, the monitored specific environmental condition is the presence of 2,3-pentanedione.

In another specific exemplary embodiment of the optical sensor, the monitored specific environmental condition is the presence of trimellitic anhydride.

In another specific exemplary embodiment of the optical sensor, the monitored specific environmental condition is the presence of phthalic anhydride.

In another specific exemplary embodiment of the optical sensor, the monitored specific environmental condition is the presence of maleic anhydride.

In another specific exemplary embodiment of the optical sensor, the monitored specific environmental condition is the presence of ionic platinum.

In another specific exemplary embodiment of the optical sensor, the monitored specific environmental condition is the presence of glucose.

In another specific exemplary embodiment of the optical sensor, the monitored specific environmental condition is pH level in breath condensate.

Another exemplary embodiment of the present invention comprises a method of monitoring an environmental condition with an optical sensor comprising a perfluorosulfonate ionomer membrane comprising a solution, wherein the solution comprises a transition metal-free dye component, the method comprising the steps of exposing the optical sensor in an environment and examining the optical sensor for color shift associated with a specific environmental condition.

In a specific exemplary embodiment of the method of monitoring an environmental condition with an optical sensor, examining comprises visually inspecting the optical sensor.

In another specific exemplary embodiment of the method of monitoring an environmental condition with an optical sensor, examining comprises spectroscopic analysis.

In another specific exemplary embodiment of the method of monitoring an environmental condition with an optical sensor, monitoring occurs continuously at ambient conditions.

Another specific exemplary embodiment of the method of monitoring an environmental condition with an optical sensor further comprises emitting an alarm when the optical sensor indicates a specific environmental condition.

Another exemplary embodiment of the present invention comprises a method of manufacturing an optical sensor for monitoring an environmental condition, the method comprising the steps of preparing a solution, wherein the solution comprises a transition metal-free dye component; immersing a perfluorosulfonate ionomer membrane in the solution; and removing the membrane after it has absorbed the solution.

In a specific exemplary embodiment of the method of manufacturing an optical sensor, preparing the solution comprises dissolving an aromatic diamine in alcohol. In a more specific embodiment, the aromatic diamine comprises 3,4-diaminobenzophenone.

In another specific exemplary embodiment of the method of manufacturing an optical sensor, preparing the solution comprises dissolving an azo-based dye in alcohol.

In another specific exemplary embodiment of the method of manufacturing an optical sensor, preparing the solution comprises dissolving benzene-1,3-diol in alcohol.

Example 1

In this example, a solution comprising a transition metal-free dye component is prepared by dissolving 120 mg of 3,4-diaminobenzophenone in 12.5 ml of ethanol. A PFSI membrane (e.g., Nafion® 1100EW, available from DuPont™) is immersed in the solution for at least 24 hours, until no further color change is observed. Before immersion, the membrane is transparent. When removed from the solution, the membrane is bright red.

A diacetyl solution is prepared by combining 5 microliters of diacetyl and 0.5 ml of water together. Approximately 5 microliters of the diacetyl solution is then transferred with a pipette into a 500 ml round bottom flask.

The dyed, bright red PFSI membrane, now an optical sensor, is tied with parafilm to one end of a gold-coated stainless steel strip and suspended in the flask above the diacetyl solution contained within the flask. The flask is immediately sealed with a rubber stopper, which pins the steel strip against the mouth of the flask and leaves the optical sensor suspended above the diacetyl solution. The stopper is sealed with parafilm.

The bottom of the flask is heated with a hot plate to vaporize the diacetyl solution and expose the optical sensor to 30 ppm diacetyl vapor. The flask is removed from the hot plate after 15 minutes. After exposure to the diacetyl vapor, the PFSI membrane is dark red. The color shift from bright red, before diacetyl exposure, to dark red, after diacetyl exposure, is irreversible.

Figure 2:
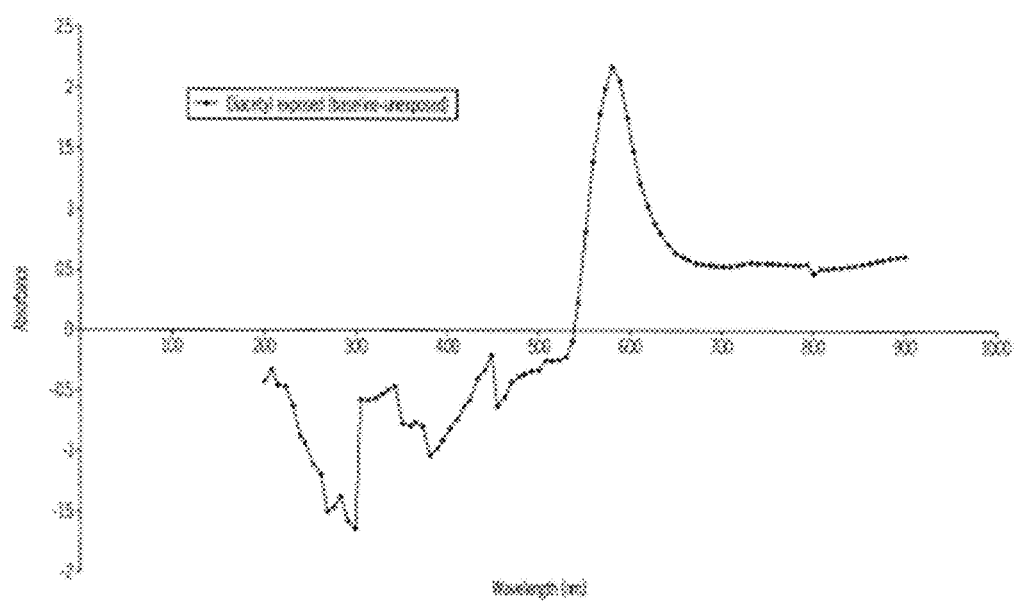
FIG. 2 is a graphical representation of the UV/VIS spectrum of an optical sensor comprising a PFSI membrane and 3,4-diaminobenzophenone after exposure to a 30 ppm diacetyl vapor (after subtraction of the optical sensor spectrum).
Figure 3:
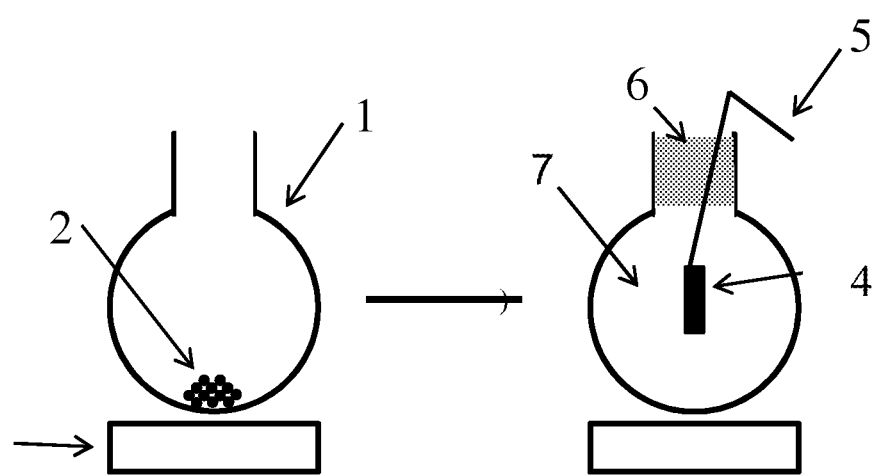
FIG. 3 is a schematic of the optical sensor showing, at left, a flask (1), TMA crystals (2), and a heating mantle (3); at right is a membrane (4), a steel strip (5), a stopper (6) and TMA vapor (7).

FIG. 1 illustrates the UV/VIS spectrum of the optical sensor following exposure to the diacetyl vapor, after subtraction of the optical sensor spectrum. A prominent peak occurs at about 590 nm, a substantial shift from the pre-exposure peak of about 350 nm.

Example 2

In this example, a solution comprising a transition metal-free dye component is prepared by dissolving 8 mg of 3,4-diaminobenzophenone in 12.5 ml of ethanol. A PFSI membrane is immersed in the solution for at least 24 hours, until no further color change is observed. When removed from the solution, the membrane is yellow-green.

The dyed, yellow-green PFSI membrane, now an optical sensor, is exposed to 30 ppm diacetyl vapor using the procedure set forth in Example 1. After exposure to the diacetyl vapor, the PFSI membrane is dark green. The color shift from yellow-green, before diacetyl exposure, to dark green, after diacetyl exposure, is irreversible.

Example 3

In this example, a solution comprising a transition metal-free dye component is prepared by dissolving 24 mg of 3,4-diaminobenzophenone in 12.5 ml of ethanol. A PFSI membrane is immersed in the solution for at least 24 hours, until no further color change is observed. When removed from the solution, the membrane is light orange.

The dyed, light orange PFSI membrane, now an optical sensor, is exposed to 30 ppm diacetyl vapor using the procedure set forth in Example 1. After exposure to the diacetyl vapor, the PFSI membrane is dark orange. The color shift from light orange, before diacetyl exposure, to dark orange, after diacetyl exposure, is irreversible.

Example 4

In this example, a solution comprising a transition metal-free dye component is prepared by dissolving 60 mg of 3,4-diaminobenzophenone in 12.5 ml of ethanol. A PFSI membrane is immersed in the solution for at least 24 hours, until no further color change is observed. When removed from the solution, the membrane is light red.

The dyed, light red PFSI membrane, now an optical sensor, is exposed to 30 ppm diacetyl vapor using the procedure set forth in Example 1. After exposure to the diacetyl vapor, the PFSI membrane is dark red. The color shift from light red, before diacetyl exposure, to dark red, after diacetyl exposure, is irreversible.

Example 5

In this example, a solution comprising a transition metal-free dye component is prepared by dissolving 8 mg of 3,4-diaminobenzophenone in 12.5 ml of ethanol. A PFSI membrane is immersed in the solution for at least 24 hours, until no further color change is observed. When removed from the solution, the membrane is light green.

Different portions of the dyed, light green PFSI membrane, now an optical sensor, are exposed to various concentrations of diacetyl vapor (5, 10, 15 and 20 ppm) using the procedure set forth in Example 1, with the exception that portions of the optical sensor exposed to one concentration of diacetyl vapor are not exposed to other concentrations. Exposure of the optical sensor to the various concentrations of diacetyl vapor results in the color of the exposed portions shifting from light green to darker green, with increased concentrations of diacetyl vapor resulting in darker shades of green. A color shift is observed even on the portion of the optical sensor exposed to a diacetyl vapor concentration of 5 ppm.

Example 6

In this example, two optical sensors are prepared according to the procedure described in a Example 1. Both optical sensors are bright red. One optical sensor is exposed to a 10 ppm concentration of vapor of the diacetyl isomer, vinyl acetate and the other optical sensor is exposed to a 10 ppm concentration of vapor of the diacetyl-like diketone, 2,3-pentanedione, using the procedure set forth in Example 1. The optical sensor exposed to vinyl acetate exhibits a color shift from bright red to reddish-brown; the optical sensor exposed to 2,3-pentanedione exhibits a color shift to a darker shade of red than that of the pre-exposure optical sensor.

Example 7

In this example, multiple solutions comprising transition metal-free dye components are prepared by dissolving 120 mg of 3,4-diaminobenzophenone in 12.5 ml of 50/50 ethanol/water solutions (by volume) at various pH levels. A separate PFSI membrane is immersed into each solution for a period of 24 hours. The PFSI membranes are optically sensitive to pH level. For example, the PFSI membrane immersed in the solution with a pH level of 3 exhibited a color shift to bright red; the PFSI membrane immersed in the solution with a pH level of 6 exhibited a color shift to brown-yellow; the PFSI membrane immersed in the solution with a pH level of 8.5 exhibited a color shift to olive green.

Example 8

In this example, a solution comprising a transition metal-free dye component is prepared by dissolving 0.12 grams of benzene-1,3-diol (also known as resorcinol) in 12.5 ml of ethanol. A PFSI membrane is immersed in the solution for at least 24 hours. No color change occurs; the PFSI membrane is still transparent.

The PFSI membrane comprising benzene-1,3-diol, now an optical sensor, is tied with parafilm to one end of a gold-coated stainless steel strip. The optical sensor is suspended in a 500 ml round bottom flask and above approximately 0.01 grams of trimellitic anhydride crystals contained within the flask. The flask is immediately sealed with a rubber stopper, which pins the steel strip against the mouth of the flask and leaves the optical sensor suspended above the TMA crystals. The stopper is sealed with parafilm.

The bottom of the flask is heated through a heating mantle until the TMA crystals vaporize, yielding a TMA vapor concentration of about 0.25% by volume. After exposure to TMA, the PFSI membrane is brownish yellow.

Example 9

In this example, three optical sensors are prepared according to the procedure described in Example 8. Using the procedure set forth in Example 1, one optical sensor is exposed to a 10 ppm TMA vapor, one optical sensor is exposed to a 10 ppm phthalic anhydride vapor, and one optical sensor is exposed to 10 ppm maleic anhydride vapor. The optical sensors exhibit a unique response to each compound. The optical sensor exposed to TMA exhibits a color shift from transparent to light yellow-brown; the optical sensor exposed to phthalic anhydride exhibits a color shift from transparent to tan-light brown; the optical sensor exposed to maleic anhydride exhibits a color shift from transparent to brown.

Example 10

In this example, a solution comprising a transition metal-free dye component is prepared by dissolving 120 mg of 3,4-diaminobenzophenone in 12.5 ml of ethanol. A PFSI membrane is immersed in the dye solution for at least 24 hours, until no further color change is observed. Before immersion, the membrane is transparent. When removed, the membrane is red.

A 1000 ppm platinum concentration solution is prepared by dissolving 0.03 grams of hexachloroplatinic acid ($H_2PtCl_6 \cdot 6H_2O$) in 10 ml of 0.1N HCl. The platinum solution is transferred to a 500 ml round bottom flask.

The dyed, red PFSI membrane, now an optical sensor, is tied with parafilm at one end of a gold-coated stainless steel strip and immersed in the platinum solution. The platinum solution is heated to 70-75° C. through a heating mantle. The heating temperature replicates the typical operating temperature of PEM fuel cells. After 15 minutes, the optical sensor is removed from the platinum solution and rinsed with deionized water. After exposure, the optical sensor is black. The color shift, from red, before platinum exposure, to black, after platinum exposure, is irreversible.

Example 11

In this example, two optical sensors are prepared according to the procedure described in Example 10. One optical sensor is immersed in 100 ppm platinum solution; the other is immersed in 10 ppm platinum solutions using the procedure described in Example 10. The magnitude of the color shift of the optical sensor is correlated to the platinum concentration of the platinum solution. The optical sensor immersed in the 100 ppm platinum concentration exhibits a color shift from red to dark brown; the optical sensor immersed in the 10 ppm platinum concentration exhibits a color shift from red to light brown.

Example 12

In this example, two PFSI membranes comprising 3,4-diaminobenzophenone are prepared as in Example 1. The dyed, red PFSI membrane is an optical sensor.

An aqueous solution comprising de-ionized water and 3% glucose by volume is prepared and heated to 80° C. One optical sensor is immersed in the solution. After exposure, the optical sensor is brown. The color shift from red, before exposure to glucose, to brown, after exposure to glucose, is irreversible. FIG. 2 is a black-and-white photograph of the unexposed optical sensor on the left and the exposed optical sensor on the right.

While the invention has been described with reference to certain embodiments, it is understood by those skilled in the art that various changes may be made and equivalents may be substituted without departing from the scope of the invention, as that scope is defined by the claims. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method of monitoring for presence of a target compound in an environment in gas phase via an optical sensor comprising a solid state perfluorosulfonate ionomer (PFSI) membrane comprising perfluorosulfonic acid functional groups and benzene-1,3-diol immobilized in the membrane within a proximity to the perfluorosulfonic acid functional groups necessary to effectuate acid catalysis of a reaction between the benzene-1,3-diol and the target compound sufficient to produce a detectable color shift on the PFSI membrane when the membrane is exposed to the target compound in gas phase, the method comprising:
   exposing the optical sensor to an environment; and
   examining the optical sensor for a detectable color shift indicating presence of the target compound.

2. The method according to claim 1, wherein the target compound is selected from the group consisting of trimellitic anhydride, diacetyl, vinyl acetate, 2,3-pentanedione, phthalic anhydride, maleic anhydride, ionic platinum, glucose, and combinations thereof.

3. The method according to claim 1, wherein the examining comprises visually inspecting the optical sensor.

4. The method according to claim 1, wherein the examining comprises analyzing the optical sensor using portable or remote spectroscopic analysis.

5. The method according to claim 1, wherein the monitoring occurs continuously at ambient conditions.

6. The method according to claim 1, further comprising emitting an alarm when a color shift indicating presence of the target compound is observed.

7. A method of manufacturing a solid state optical sensor for detecting a target compound in gas phase in an environment, the method comprising the steps of:
   preparing a solution comprising benzene-1,3-diol;
   immersing a perfluorosulfonate ionomer (PFSI) membrane in the solution;
   permitting the PFSI membrane to absorb the organic compound; and
   removing the PFSI membrane from the solution,
   wherein the PFSI membrane comprising the absorbed benzene-1,3-diol comprises a solid state optical sensor that produces an irreversible and detectable color shift upon exposure to the target compound in gas phase.

8. The method according to claim 7, wherein preparing a solution comprises dissolving the benzene-1,3-diol in alcohol.

9. The method according to claim 8, wherein preparing the solution comprises dissolving 0.12 grams of benzene-1,3-diol in 12.5 ml ethanol.

10. An optical sensor for detecting a target compound present in an environment in gas phase, the optical sensor comprising:
   a solid state perfluorosulfonate ionomer (PFSI) membrane comprising perfluorosulfonic acid functional groups; and
   benzene-1,3-diol immobilized in the membrane within a proximity to the perfluorosulfonic acid functional groups necessary to effectuate acid catalysis of a reaction between the benzene-1,3-diol and the target compound sufficient to produce a detectable color shift on the PFSI membrane when the membrane is exposed to the target compound in gas phase.

* * * * *